United States Patent
Kanazawa et al.

(10) Patent No.: US 9,333,299 B2
(45) Date of Patent: May 10, 2016

(54) TWO-CHAMBER TYPE COMBINED CONTAINER SYRINGE

(71) Applicant: ARTE CORPORATION, Tokyo (JP)

(72) Inventors: Atsushi Kanazawa, Takahagi (JP);
Katsuyoshi Tuchida, Takahagi (JP);
Junichi Komuro, Kitaibaraki (JP); Seiji Shimazaki, Takahagi (JP)

(73) Assignee: ARTE CORPORATION, Tokyo (JP)

(*) Notice: Subject to any disclaimer, the term of this patent is extended or adjusted under 35 U.S.C. 154(b) by 191 days.

(21) Appl. No.: 14/180,353

(22) Filed: Feb. 13, 2014

(65) Prior Publication Data

US 2014/0316342 A1 Oct. 23, 2014

(30) Foreign Application Priority Data

Feb. 15, 2013 (JP) ................. 2013-028315

(51) Int. Cl.
*A61M 5/19* (2006.01)
*A61M 5/28* (2006.01)
*A61M 5/315* (2006.01)
*A61M 5/31* (2006.01)

(52) U.S. Cl.
CPC ............... *A61M 5/19* (2013.01); *A61M 5/284* (2013.01); *A61M 5/31501* (2013.01); *A61M 5/3137* (2013.01); *A61M 2005/3132* (2013.01)

(58) Field of Classification Search
CPC .................. A61M 5/19; A61M 5/284
See application file for complete search history.

(56) References Cited

U.S. PATENT DOCUMENTS

| 2,591,046 | A | | 4/1952 | Brown | |
|---|---|---|---|---|---|
| 4,439,184 | A | * | 3/1984 | Wheeler | A61M 3/005 604/191 |
| 4,496,344 | A | * | 1/1985 | Kamstra | A61M 5/284 604/191 |
| 4,792,329 | A | | 12/1988 | Schreuder | |

(Continued)

FOREIGN PATENT DOCUMENTS

| EP | 2676689 A1 | 12/2013 |
|---|---|---|
| JP | B-04-046152 B | 7/1992 |

(Continued)

OTHER PUBLICATIONS

Office Action in Japanese application No. 2013-028315 dated Jun. 4, 2013.
Search Report in EP application No. 14155031.9 dated Jun. 25, 2014.

*Primary Examiner* — Aarti B Berdichevsky
(74) *Attorney, Agent, or Firm* — Nixon Peabody LLP

(57) ABSTRACT

A two-chamber type combined container-syringe includes an outer tube (10) formed in a tubular shape having a uniform inner diameter about an axis (O) thereof throughout the axis direction and provided with a bypass groove (11a) concaved from an inner circumferential surface in a portion in the axis direction, wherein the inner diameter of the outer tube (10) is 6.0 mm or more and 10.0 mm or less, the plurality of bypass grooves are formed in the circumferential direction of the axis at intervals, a cross-sectional area of the bypass groove perpendicular to the axis is 0.13% or more and 0.24% or less of an inner circumferential cross-sectional area of the outer tube perpendicular to the axis, and a depth of the bypass groove concaved from the inner circumferential surface is 2.7% or more and 3.8% or less of the inner diameter of the outer tube. As a result, solution can smoothly flow through the bypass groove, and an amount of solution remaining in the bypass groove can be reduced.

7 Claims, 6 Drawing Sheets

(56) References Cited

U.S. PATENT DOCUMENTS

| | | | | |
|---|---|---|---|---|
| 5,788,670 A | * | 8/1998 | Reinhard | A61M 5/3129 604/191 |
| 5,935,101 A | * | 8/1999 | Kato | A61M 5/284 604/181 |
| 6,966,897 B2 | * | 11/2005 | Shimazaki | A61M 5/3129 604/110 |
| 7,311,692 B2 | * | 12/2007 | Kato | A61M 5/284 604/82 |
| 7,699,811 B2 | * | 4/2010 | Hasegawa | A61M 5/3134 604/122 |
| 8,517,983 B2 | * | 8/2013 | Kakiuchi | A61M 5/284 604/89 |

FOREIGN PATENT DOCUMENTS

| | | |
|---|---|---|
| JP | B-2942835 B | 8/1999 |
| JP | B-4439577 B | 3/2010 |
| JP | B-4757951 B | 8/2011 |
| JP | B-5081330 B | 11/2012 |

\* cited by examiner

TWO-CHAMBER TYPE COMBINED CONTAINER SYRINGE

BACKGROUND OF THE INVENTION

1. Field of the Invention

The present invention relates to a two-chamber type combined container-syringe, in which a medicinal solution is previously filled and stored, and the can be taken out from a package upon use and instantly used.

Priority is claimed on Japanese Patent Application No. 2013-28315, filed Feb. 15, 2013, the content of which is incorporated herein by reference.

2. Description of Related Art

A combined container-syringe, since a medicinal solution is previously filled, can be taken out from a package to be instantly used in a medical institute without complicated operation. The combined container-syringe is widely employed in many hospitals and clinics due to good convenience and large contribution to reduction in work of health care providers such as doctors, nurses, and so on.

Conventionally, a two-chamber type combined container-syringe in which a preparation and solution are separately filled is known as a kind of the combined container-syringe (for example, refer to Japanese Patent No. 1759157).

In the two-chamber type combined container-syringe, a front stopper is fitted into a distal end side of an outer tube and an end stopper is fitted into a rear end side, and the inside of the outer tube is divided into two front and rear chambers by a middle stopper fitted into a central section of the outer tube. In addition, a bypass groove is formed at a portion of the outer tube closer to the distal end side than the middle stopper such that a portion of an inner circumferential surface of the outer tube swells outward. Further, a powdered preparation is sealed in the front chamber of the distal end side of the middle stopper, and the distal end is sealed by the front stopper. Meanwhile, solution is sealed in the rear chamber of the rear end side of the middle stopper, and the rear end is sealed by the end stopper. In addition, a plunger rod is connected to the rear end of the end stopper.

When the two-chamber type combined container-syringe having the above-mentioned configuration is used, the end stopper is advanced in the outer tube by pushing the plunger rod into the outer tube. Then, as a pressing force is applied to the middle stopper via the solution by advancement of the end stopper, the middle stopper is also advanced with the advancement of the end stopper. Then, when the middle stopper arrives at the bypass groove, the front and rear chambers of the middle stopper come in communication with each other via a swelling portion of the bypass groove. Accordingly, the solution in the rear chamber flows into the front chamber, and an injection drug is prepared by mixing the solution and the preparation of the front chamber.

Here, for example, in Japanese Patent No. 2942835, the combined container-syringe in which the plurality of above-mentioned bypass grooves are formed in an axial direction of an outer tube is disclosed.

That is, in Japanese Patent No. 2942835, the combined container-syringe in which a plurality of bypass grooves are formed in an inner circumferential surface of the outer tube to continue through the entire region thereof in a circumferential direction is disclosed. In addition, in this document, the combined container-syringe in which a portion between the bypass grooves neighboring in the circumferential direction protrudes toward an inner diameter side of the outer tube more than an inner circumferential surface of the outer tube is also disclosed.

Furthermore, in the specification of U.S. Pat. No. 2,591, 046, the combined container-syringe in which a plurality of bypass grooves are formed in an inner circumferential surface of an outer tube at intervals in a circumferential direction is disclosed. In this combined container-syringe, the bypass groove has a rectangular cross-sectional shape along a direction perpendicular to an axis of the outer tube, and the depth of the bypass groove from the inner circumferential surface of the outer tube is set to be near the outer circumferential surface of the outer tube.

In the above-mentioned two-chamber type combined container-syringe, in order to appropriately mix the solution and the preparation, the middle stopper must be stay at a region in the outer tube at which the bypass groove is present, until flowing of all of the solution of the rear chamber into the front chamber is terminated. Furthermore, depending on a kind of the preparation filled in the front chamber, all of the solution of the rear chamber must be rapidly flow into the front chamber.

However, when a cross-sectional area of the bypass groove is too small, even when the plunger rod is further pushed in a state in which the middle stopper arrives at the bypass groove, since flow resistance of the solution passing through the bypass groove is large, the solution may not smoothly flow through the bypass groove. Accordingly, the pressing force applied to the solution via the end stopper by pushing of the plunger rod mainly contributes to the advancement of the middle stopper. As a result, even when the solution remains at the rear end of the middle stopper, the middle stopper may advance over the bypass groove.

On the other hand, when a total cross-sectional area of the plurality of bypass grooves is increased, while the flowing of the solution in the bypass groove can be accelerated, the amount of the solution remaining in the bypass groove may be increased and the strength of the outer tube may be decreased if the cross-sectional area is too large.

In consideration of the above-mentioned problems, the present invention is directed to provide a two-chamber type combined container-syringe capable of causing solution to smoothly flow through a bypass groove, reducing an amount of the solution remaining in the bypass groove, and enabling smooth sliding of a middle stopper and an end stopper without to decrease slidability of these stoppers due to the bypass.

SUMMARY OF THE INVENTION

In order to solve the problems, the present invention proposes the following means.

That is, a two-chamber type combined container-syringe according to the first aspect of the present invention includes: an outer tube formed in a tubular shape having a uniform inner diameter about an axis thereof in an axial direction and provided with a bypass groove concaved from an inner circumferential surface in a portion in the axial direction to a length slightly larger than that of a middle stopper; a front assembly installed at a distal end of the outer tube; a finger grip installed at a rear end of the outer tube; a front stopper fitted into a distal end side of the bypass groove in the outer tube; the middle stopper fitted into a rear end side of the bypass groove in the outer tube and configured to seal a preparation with the front stopper; an end stopper fitted into the rear end side of the middle stopper in the outer tube and configured to seal solution with the middle stopper; and a plunger rod inserted through the finger grip to be connected to the end stopper from the rear end side, wherein the inner diameter of the outer tube is 6.0 mm or more and 10.0 mm or less, the plurality of bypass grooves are formed in a circumferential direction of the axis at intervals, a cross-sectional area of the bypass groove perpendicular to the axis is 0.13% or more and 0.24% or less of an inner circumferential cross-sectional area of the outer tube perpendicular to the axis, a depth of the bypass groove concaved from the inner circumferential surface is 2.7% or more and 3.8% or less of the inner diameter of the outer tube.

According to the two-chamber type combined container-syringe having the above-mentioned features, since the cross-sectional area of the bypass groove is 0.13% or more and 0.24% or less of the inner circumferential cross-sectional area of the outer tube, the solution can smoothly flow through the bypass groove.

Furthermore, since the depth of the bypass groove is 2.7% or more and 3.8% or less of the inner diameter of the outer tube, a decrease in fracture strength of the outer tube can be prevented and the solution remaining in the bypass groove can be eliminated.

In the above-mentioned two-chamber type combined container-syringe, it is preferable that a sum of the cross-sectional areas of the entire bypass grooves perpendicular to the axis is 0.8% to 2.4% of an inner circumferential cross-sectional area of the outer tube perpendicular to the axis.

In the outer tube having the inner diameter of 6.0 mm or more and 10.0 mm or less, when the total cross-sectional area, which is the sum of the cross-sectional area of the plurality of bypass grooves, is less than 0.8% of the inner circumferential cross-sectional area of the outer tube, since flow resistance of the solution in the bypass groove is large, the middle stopper may advance before all of the solution flows toward the front end of the middle stopper via the bypass groove. On the other hand, in the present invention, as the total cross-sectional area of the bypass groove is set within the above-mentioned range, all of the solution of the rear chamber flows into the front chamber even when the plunger rod is rapidly pushed, and the solution remaining in the bypass groove can be eliminated without causing advancement of the middle stopper.

In addition, the two-chamber type combined container-syringe according to the second aspect of the present invention includes an outer tube formed in a tubular shape having a uniform inner diameter about an axis thereof in an axial direction and provided with a bypass groove concaved from an inner circumferential surface in a portion in the axial direction; a front assembly installed at a distal end of the outer tube; a finger grip installed at a rear end of the outer tube; a front stopper fitted into a distal end side of the bypass groove in the outer tube; a middle stopper fitted into a rear end side of the bypass groove in the outer tube and configured to seal a preparation with the front stopper; an end stopper fitted into the rear end side of the middle stopper in the outer tube and configured to seal solution with the middle stopper; and a plunger rod inserted through the finger grip to be connected to the end stopper from the rear end side, wherein the inner diameter of the outer tube is 10.1 mm or more and 18.0 mm or less, the plurality of bypass grooves are formed in a circumferential direction of the axis at intervals, a cross-sectional area of the bypass groove perpendicular to the axis is 0.105% or more and 0.160% or less of an inner circumferential cross-sectional area of the outer tube perpendicular to the axis, and a depth of the bypass groove concaved from the inner circumferential surface is 2.1% or more and 3.3% or less of the inner diameter of the outer tube.

According to the two-chamber type combined container-syringe having the above-mentioned features, since the cross-sectional area of the bypass groove is 0.105% or more and 0.160% or less of the inner circumferential cross-sectional area of the outer tube, the solution can smoothly flow through the bypass groove.

Further, since the depth of the bypass groove is 2.1% or more and 3.3% or less of the inner diameter of the outer tube, a decrease in fracture strength of the outer tube can be prevented and the solution remaining in the bypass groove can be eliminated.

In the above-mentioned two-chamber type combined container-syringe, a sum of the cross-sectional areas of the entire bypass grooves perpendicular to the axis may be 0.65% to 2.15% of an inner circumferential cross-sectional area of the outer tube perpendicular to the axis.

In the outer tube having the inner diameter of 10.1 mm or more and 18.0 mm or less, when the total cross-sectional area, which is the sum of the cross-sectional area of the plurality of bypass grooves, is less than 0.65% of the inner circumferential cross-sectional area of the outer tube, since flow resistance of the solution in the bypass groove is large, the middle stopper may advance before all of the solution flows toward the front end of the middle stopper via the bypass groove. On the other hand, in the present invention, as the total cross-sectional area of the bypass groove is set within the above-mentioned range, the solution remaining in the bypass groove can be eliminated without movement of the middle stopper to a forward side of the bypass groove before all of the solution flows into the front chamber.

In addition, in the two-chamber type combined container-syringe, an interval of the bypass grooves neighboring in the circumferential direction of the axis may be within a range of 2.0 mm to 7.3 mm.

Here, in the outer tube having the inner diameter of 10.1 mm or more and 18.0 mm or less, when the interval between the bypass grooves is less than 2.0 mm, a smooth surface between the bypass grooves is remarkably reduced, and bad influence is applied to slidability of the stopper sliding along the bypass section. In addition, in the outer tube having the inner diameter of 6.0 mm or more and 10.0 mm or less, when the interval between the bypass grooves is larger than 7.3 mm, the number of bypass grooves that can be formed is four or less, and the solution cannot be uniformly introduced from surroundings of the preparation.

On the other hand, in the present invention, since the interval between the bypass grooves is within the range of 2.0 mm to 7.3 mm, this inconvenience can be overcome.

In addition, in the two-chamber type combined container-syringe, the cross-sectional shape of the bypass groove perpendicular to the axis may be any one of a triangular shape, a trapezoidal shape, a semi-circular shape, or a combination thereof.

Here, when the cross-sectional shape of the bypass groove is rectangular, the fracture strength of the outer tube is remarkably reduced by sharp corners of the rectangular shape, and the solution is likely to remain in the bottom section of the bypass groove. On the other hand, in the present invention, as the cross-sectional shape of the bypass groove is one of these shapes, the solution remaining in the bypass groove can be further eliminated without decreasing the strength of the outer tube.

In addition, in the two-chamber type combined container-syringe, the outer tube may be formed of glass or a synthetic resin.

In the two-chamber type combined container-syringe in which the plurality of bypass grooves are formed, any material such as glass or a plastic can be employed for the outer tube according to properties of medical and pharmaceutical products filled and stored in the outer tube.

According to the two-chamber type combined container-syringe of the present invention, since the solution can smoothly flow through the bypass groove, advancement of the middle stopper before introduction of the solution toward the front end of the middle stopper can be prevented. In addition, a decrease in fracture strength of the outer tube can be prevented and the amount of solution remaining in the bypass groove can be reduced.

DETAILED DESCRIPTION OF THE PREFERRED EMBODIMENTS

Hereinafter, a two-chamber type combined container-syringe according to an embodiment of the present invention will be described in detail with reference to the accompanying drawings.

Figure 1:
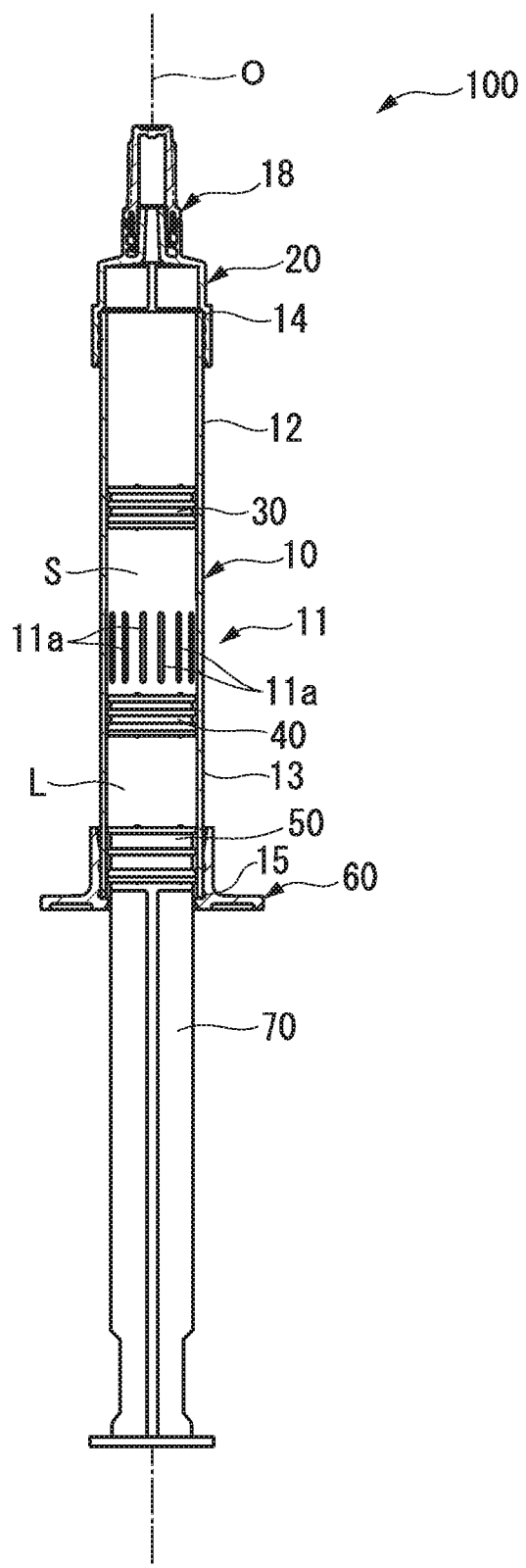
FIG. 1 is a longitudinal cross-sectional view of the two-chamber type combined container-syringe according to the embodiment, showing a state in which a preparation and solution are filled and the syringe is assembled.
Figure 2:
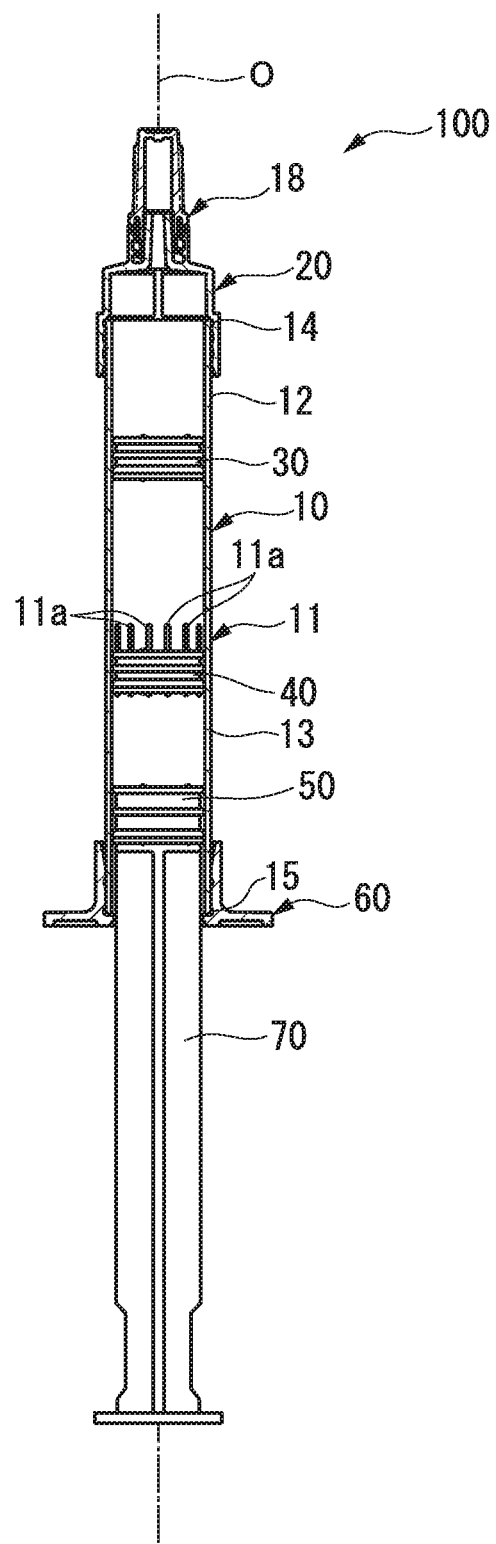
FIG. 2 is a longitudinal cross-sectional view of the two-chamber type combined container-syringe according to the embodiment, showing a state in which a middle stopper arrives at a bypass groove.

As shown in FIGS. 1 and 2, a two-chamber type combined container-syringe 100 includes an outer tube 10, a front assembly 18, a front stopper 30, a middle stopper 40, an end stopper 50, a finger grip 60, and a plunger rod 70. A preparation S and solution L, which are to be mixed to prepare an injection drug, are separately filled in the two-chamber type combined container-syringe 100.

The outer tube 10 is formed of transparent glass or a synthetic resin, and forms a substantially tubular shape extending along an axis O. In a substantially central section in the axis O direction of the outer tube 10, a bypass groove 11a is formed to be concaved outward in a radial direction throughout a dimension slightly larger than a length in an axial direction of the middle stopper 40 in the axis O direction of the inner circumferential surface of the outer tube 10. In addition, a position in the axis O direction of the bypass groove 11a may be appropriately set according to design.

Further, a region in the axial direction of the outer tube 10 in which the bypass grove 11a is present is a bypass section 11. Then, a tubular portion of the distal end side of the bypass section of the outer tube 10 is a distal end side tubular section 12, and a tubular portion of the rear end side of the bypass section 11 is a rear end side tubular section 13. That is, in the outer tube 10, the distal end side tubular section 12 is disposed at the distal end side with reference to the bypass section 11 as a boundary, and the rear end side tubular section 13 is disposed at the rear end side. In other words, in the outer tube 10, a region of the distal end side is the distal end side tubular section 12, a region of the central section is the bypass section 11, and a region of the rear end side is the rear end side tubular section 13.

In addition, in the distal end outer circumference of the outer tube 10, a distal end side ring-shaped protrusion 14 protruding outward in the radial direction is formed throughout the entire region in the circumferential direction. Further, even in the rear end outer circumference of the outer tube 10, a rear end side ring-shaped protrusion 15 protruding outward in the radial direction is formed throughout the entire region in the circumferential direction.

Figure 3:
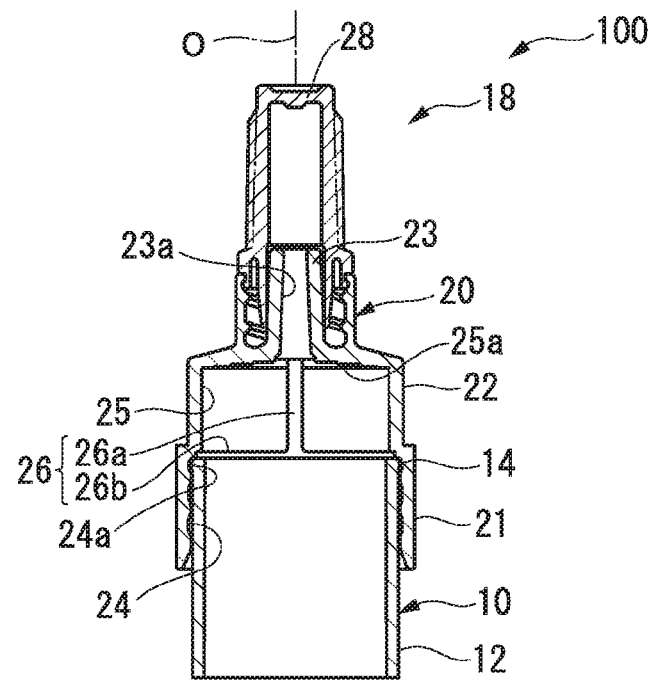
FIG. 3 is an enlarged view of the distal end section of the two-chamber type combined container-syringe according to the embodiment.

As shown in FIG. 3, a hub luer-lock 20 is formed of a transparent synthetic resin having appropriate stiffness, and forms a multi-stage columnar shape about the axis O. The hub luer-lock 20 includes a base end section 21 having a tubular shape, a tubular section 22 coupled to the distal end side of the base end section 21 to be reduced in diameter in one step, and a luer tip 23 formed at a further distal end side of the tubular section 22 with a diameter smaller than that of the tubular section 22.

A fitting hole 24 opened at the rear end side of the hub luer-lock 20 is formed inside the base end section 21, and a bypass chamber 25 having a bottomed hole shape is formed at a forward side of the fitting hole 24, i.e., inside the tubular section 22. A place corresponding to the bottom section of the bypass chamber 25 provides a front end surface 25a which is configured to abut the distal end of the front stopper 30. The front end surface 25a is formed as a conical shape or a concentric circular shape having a diameter which gradually reduces toward the forward side.

In addition, an introduction hole 23a passing along the axis O is formed in the luer tip 23, and the introduction hole 23a has one end side opened at the distal end of the luer tip 23 and the other end side opened at a center of the front end surface 25a of the bypass chamber 25. An injection needle extending toward the distal end side along the axis O is attached to the one end side, i.e., the distal end side of the introduction hole 23a in a communication state.

The fitting hole 24 is a hole formed to attach the hub luer-lock 20 to the outer tube 10, and an inner diameter thereof is formed to be substantially equal to an outer diameter of the outer tube 10. As the fitting hole 24 is fitted onto the distal end of the outer tube 10, the hub luer-lock 20 is attached to the distal end side of the outer tube 10.

In addition, a ring-shaped groove 24a concaved in an annular shape about the axis O is formed in a front end section of an inner circumferential wall of the fitting hole 24. When the hub luer-lock 20 is attached to the distal end side of the outer tube 10, as the distal end side ring-shaped protrusion 14 of the outer tube 10 is fitted into the ring-shaped groove 24a, the hub luer-lock 20 is securely fixed and integrated with the outer tube 10 in an air-tight/liquid-tight manner.

The bypass chamber 25 is a bottomed hole having an inner diameter reduced to be smaller than that of the fitting hole 24 by one step, and a groove section 26 is formed at the inner circumferential wall. The groove section 26 is constituted by a linear groove 26a and an annular groove 26b.

The plurality of linear grooves 26a are formed in the inner wall surface of the bypass chamber 25 to extend parallel to the axis O at equal intervals in the circumferential direction, and distal end sides of the linear grooves 26a are extending from the inner wall surface of the bypass chamber 25 to the front end surface 25a and connected to the introduction holes 23a formed in the luer tip 23.

In addition, the annular groove 26b is an annular groove extending about the axis O in the circumferential direction, and is formed in the inner wall surface of the bypass chamber 25 and near a boundary between the bypass chamber 25 and the fitting hole 24. The annular groove 26b is connected to the rear ends of the plurality of linear grooves 26a, and thus the linear grooves 26a are connected to each other via the annular groove 26b respectively.

A cap 28 is attached to the luer tip 23 of the hub luer-lock 20 having the above-mentioned configuration. The front assembly 18 is constituted by the hub luer-lock 20 and the cap 28.

Figure 4:
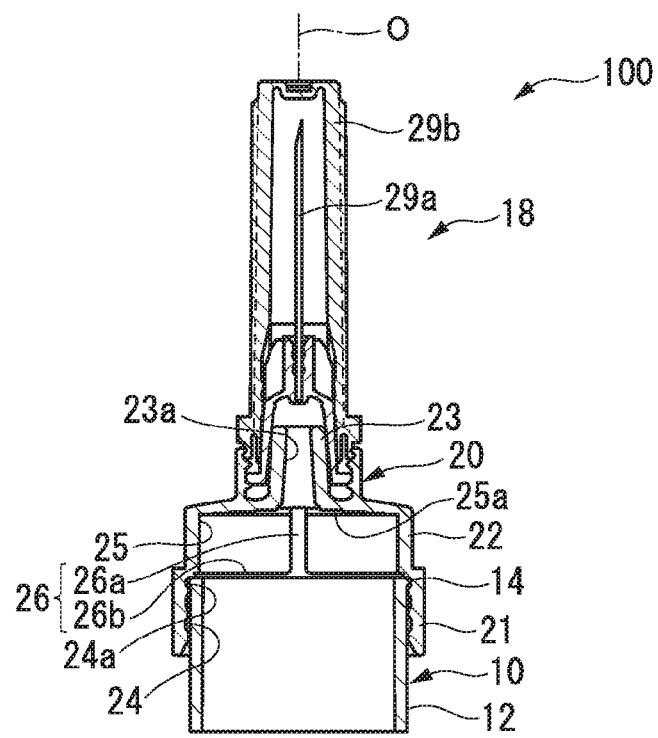
FIG. 4 is a view showing another example of the distal end section of the two-chamber type combined container-syringe according to the embodiment.

In addition, as shown in FIG. 4, instead of the cap 28, an injection needle 29a is attached to the luer tip 23 of the hub luer-lock 20, and a protector 29b is attached to the luer tip 23 to surround the injection needle 29a. In an example of FIG. 4, the front assembly 18 is constituted by the hub luer-lock 20, the injection needle 29a and the protector 29b.

The front stopper 30, the middle stopper 40 and the end stopper 50 are molded of medical rubber having corrosion resistance against the preparation S, the solution L and the injection drug M, and form a substantially columnar shape disposed about the axis O and having an outer diameter slightly larger than the inner diameter of the outer tube 10.

The front stopper 30 is inserted into the distal end side of the bypass groove 11a in the outer tube 10, i.e., the distal end side tubular section 12.

In addition, the middle stopper 40 is inserted into the rear end side of the bypass groove 11a in the outer tube 10, i.e., the rear end side tubular section 13. In particular, the middle stopper 40 according to the embodiment is disposed such that the distal end of the middle stopper 40 is disposed at a boundary between the rear end side tubular section 13 and the bypass groove 11a, which is the distal end of the rear end side tubular section 13. Then, the powdered preparation S is sealed in the outer tube 10 to be sandwiched between the front stopper 30 and the middle stopper 40. That is, the preparation S is filled in the front chamber partitioned by the inner circumferential surface of the outer tube 10, the rear end surface of the front stopper 30 and the distal end surface of the middle stopper 40.

The end stopper 50 is fitted into a further rear end side of the middle stopper 40 in the rear end side tubular section 13 of the outer tube 10 to be spaced an interval from the middle stopper 40 in the axis O direction. The solution L in a liquid phase is sealed to be sandwiched between the end stopper 50 and the middle stopper 40. That is, the solution L is filled in the rear chamber partitioned by the inner circumferential surface of the outer tube 10, the rear end surface of the middle stopper 40 and the distal end surface of the end stopper 50. In addition, a female screw hole (not shown) into which the plunger rod 70 (to be described below) is screwed into the rear end of the end stopper 50 is formed.

In this way, in the two-chamber type combined container-syringe 100, the preparation S and the solution L are separately sealed in the front chamber and the rear chamber partitioned by the middle stopper 40.

Figure 5:
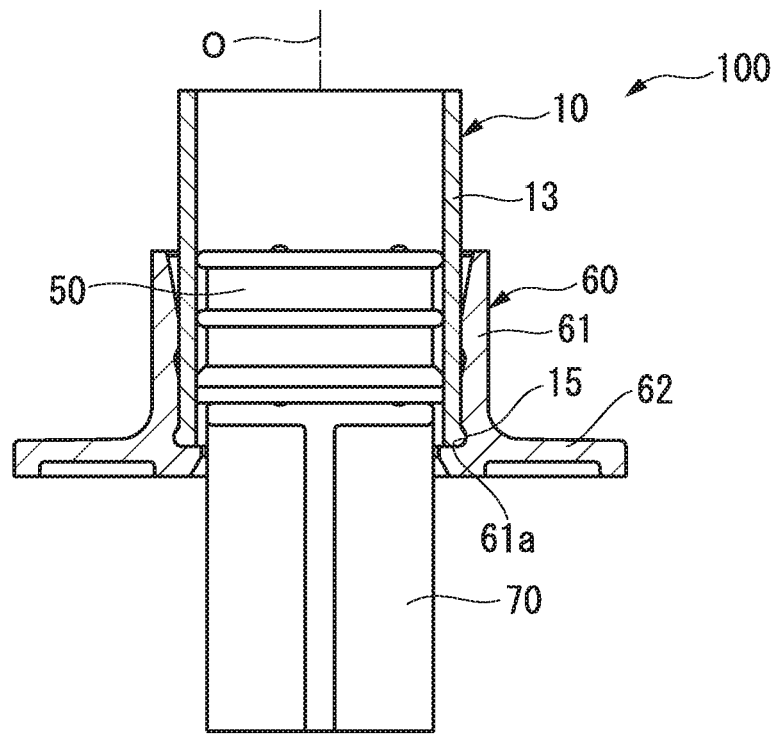
FIG. 5 is an enlarged view of the rear end section of the two-chamber type combined container-syringe according to the embodiment.

As shown in FIG. 5, the finger grip 60 includes a fitting section 61 and a flange section 62.

The fitting section 61 forms a substantially tubular shape about the axis O, and the inner circumferential side is a fitting hole 61a into which the rear end of the outer tube 10 is fitted.

The flange section 62 is overhung in the radial direction about the axis O from the vicinity of the rear end of the fitting section 61, i.e., a boundary between the fitting section 61 and the tubular section 13, and forms a substantially rectangular shape when seen in the axis O direction. The flange section 62 is configured to support a finger of a health care provider upon use of the two-chamber type combined container-syringe 100 to perform a function of allowing the health care provider to easily handle the two-chamber type combined container-syringe 100.

The plunger rod 70 has an elongated shape extending along the axis O, and a distal end thereof is connected to the end stopper 50. Accordingly, as the plunger rod is pushed into the distal end side, the end stopper 50 in the outer tube 10 can be moved toward the distal end side.

Next, a configuration of the bypass section 11 will be described in detail with reference to FIGS. 6 and 7.

Figure 6:
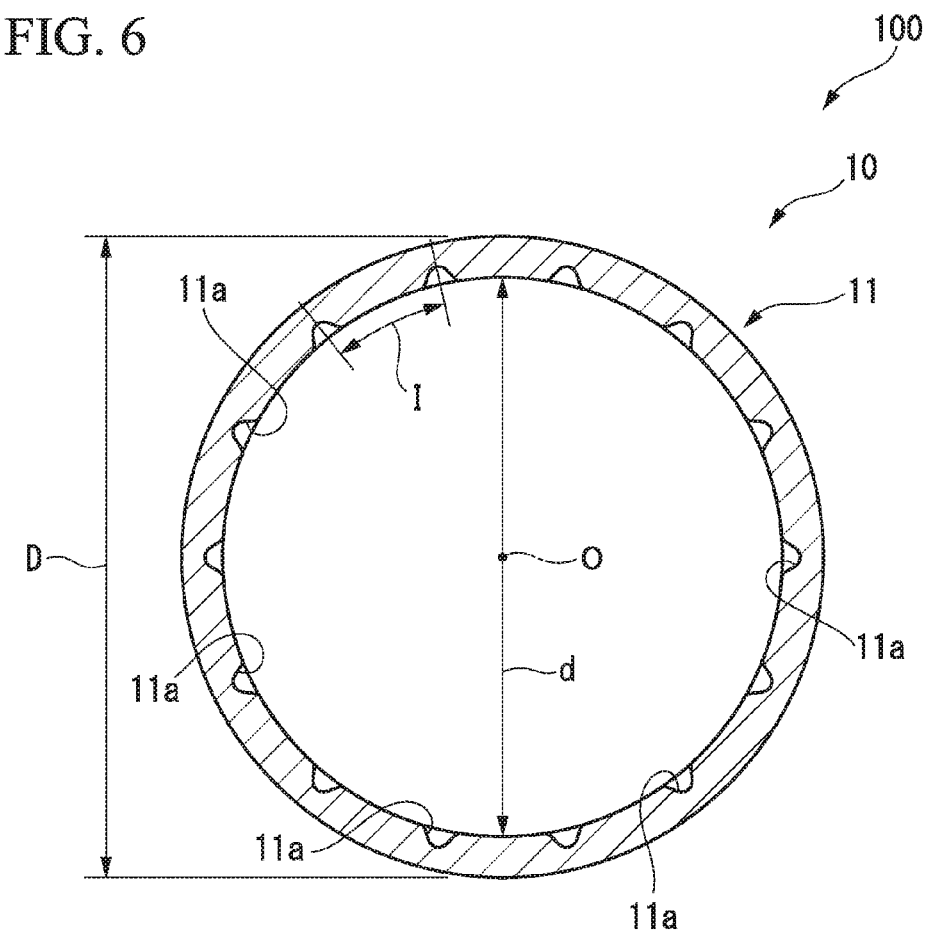
FIG. 6 is a cross-sectional view of the outer tube along a direction perpendicular to the axis thereof at the portion at which the bypass groove is present.

As shown in FIG. 6, an outer diameter D of the bypass section 11, i.e., an outer diameter D of the outer tube 10, is set to, for example, 8.65 mm, 12.5 mm, and 16.0 mm, in the case of the general two-chamber type combined container-syringe. On the other hand, an inner diameter d of the bypass section 11, i.e., an inner diameter d of the outer tube 10, is set to 6.85 mm when the outer diameter is 8.65 mm, set to 10.5 mm when the outer diameter is 12.5 mm, and set to 14.0 mm when the outer diameter is 16.0 mm.

In addition, in the embodiment, a uniform diameter is formed throughout in the axial direction with the inner circumferential surface and the outer circumferential surface of the outer tube 10.

Furthermore, the plurality of bypass grooves 11a are formed in the circumferential direction of the axis at intervals. In particular, in the embodiment, the plurality of bypass grooves 11a are formed in the circumferential direction at equal intervals. The length of each bypass groove 11a is set to be larger than the entire length in the axial direction of the middle stopper 40.

Here, in the two-chamber type combined container-syringe 100 in which the inner diameter of the outer tube 10 is set to 6.0 mm or more and 10.0 mm or less, i.e., the two-chamber type combined container-syringe 100 in which the inner diameter of the above-mentioned outer tube is 6.85 mm, it is preferable that a cross-sectional area of the bypass groove 11a perpendicular to the axis (hereinafter, simply referred to as a cross-sectional area of the bypass groove 11a) is set to 0.13% or more and 0.24% or less of an inner circumferential cross-sectional area of the outer tube 10 perpendicular to the axis (hereinafter, simply referred to as an inner circumferential cross-sectional area of the outer tube 10).

Furthermore, in the two-chamber type combined container-syringe 100, it is preferable that a sum of the cross-sectional areas of all of the bypass grooves 11a perpendicular to the axis O is set to 0.8% to 2.4% of the inner circumferential cross-sectional area of the outer tube 10 perpendicular to the axis O.

On the other hand, in the two-chamber type combined container-syringe 100 in which the inner diameter of the outer tube is 10.1 mm or more and 18.0 mm or less, i.e., the two-chamber type combined container-syringe 100 in which the inner diameter of the above-mentioned outer tube is 10.5 mm or 14.0 mm, it is preferable that the cross-sectional area of the bypass groove 11a is set to 0.105% or more and 0.160% or less of the inner circumferential cross-sectional area of the outer tube 10.

Furthermore, in the two-chamber type combined container-syringe 100, it is preferable that a sum of the cross-sectional area of the entire bypass grooves 11a perpendicular to the axis O may be set to 0.65% to 2.15% of the inner circumferential cross-sectional area of the outer tube 10 perpendicular to the axis O.

Figure 7:
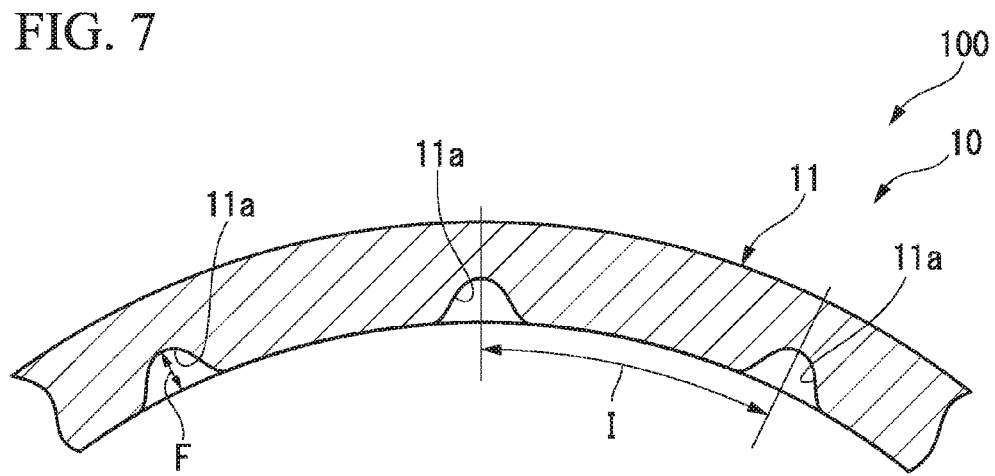
FIG. 7 is a partially enlarged view of FIG. 6.

In addition, even when the inner diameter of the outer tube 10 corresponds to any one portion of the two-chamber type combined container-syringe 100, as shown in FIG. 7, a depth F of the bypass groove 11a may be set to 65% or less of a thickness of the outer tube 10.

Furthermore, the thickness of the outer tube 10 is set to 0.9 mm, for example, when the diameter of the outer tube 10 is 8.65 mm. Furthermore, the thickness is set to 1.0 mm when the diameter of the outer tube 10 is 12.5 mm or 16.0 mm.

In addition, in the embodiment, as shown in FIG. 6, an interval I in the circumferential direction of the bypass grooves 11a neighboring each other with respect to the entire size, i.e., the interval I of the bypass grooves 11a at the center in the circumferential direction, is set to a range of 2.0 mm to 7.3 mm.

Furthermore, in the embodiment, a cross-sectional shape of the bypass groove 11a perpendicular to the axis has a substantially triangular shape. More specifically, in the cross section of the bypass groove 11a perpendicular to the axis, two sides connected to the inner circumferential surface of the outer tube 10 approach each other as they move outward in the radial direction. Accordingly, in the embodiment, the cross-sectional shape of the bypass groove 11a has substantially an isosceles triangular shape. In addition, a portion of the bypass groove 11a corresponding to a top of the cross-sectional shape has a rounded shape for the purpose of molding design.

When the two-chamber type combined container-syringe 100 having the above-mentioned configuration is used, first, the plunger rod 70 is pressed from the rear end side in a state in which the health care provider puts his/her finger on the flange section 62 of the finger grip 60. The pressing force is transmitted to the middle stopper 40 via the end stopper 50 and the solution L, i.e., the middle stopper 40 also advances in the rear end side tubular section 13 of the outer tube 10 with the advancement of the plunger rod 70 by the pressing force.

Then, when the entire length in the axis O direction of the middle stopper 40 intrudes into the bypass section 11, the front chamber of the distal end side and the rear chamber of the rear end side of the middle stopper 40 in the outer tube 10 come in communication with each other via the bypass grove 11a in the bypass section 11.

Accordingly, the solution L of the rear chamber can flow into the preparation S in the front chamber. Then, when the health care provider carefully further pushes the plunger rod 70, most of the pressing force applied to the solution L by advancement of the plunger rod 70 is converted into a pressure to introduce the solution L in the front chamber. Accordingly, the middle stopper 40 does not advance but remains in the bypass section 11, and only the solution L flows into the front chamber.

After that, when the distal end of the end stopper 50 abuts the rear end of the middle stopper 40 due to the advancement of the plunger rod 70, all of the solution L in the rear chamber is introduced into the preparation S in the front chamber, and thus the rear chamber disappears. In addition, at this time, the solution L and the preparation S are mixed in the front chamber, and the preparation S is dissolved or suspended in the solution L to prepare the injection drug by shaking the entire syringe. Then, when the plunger rod 70 is further pushed to gradually move the plunger rod 70 forward, the middle stopper 40 abutting the end stopper 50 also simultaneously advances via the end stopper 50.

Then, as a result of the front stopper 30 advancing with the advancement of the middle stopper 40, when the front stopper 30 enters the bypass chamber 25, the front chamber in which the dissolved or suspended injection drug is present comes in communication with the introduction hole 23a of the luer tip 23 via the groove section 26. Accordingly, bubbles remaining in the outer tube 10 are discharged to the outside to such that the injection drug M is in a state in which it can be introduced into the injection needle 29a, and the injection drug M can be administered to a patient.

According to the two-chamber type combined container-syringe 100 having the above-mentioned configuration, since the cross-sectional area of the bypass groove 11a is 0.13% or more and 0.24% or less, or 0.105% or more and 0.160% or less of the inner circumferential cross-sectional area of the outer tube 10, the solution can securely flow through the bypass groove 11a.

That is, when the cross-sectional area of the bypass groove 11a is less than 0.13% or 0.105% of the inner circumferential cross-sectional area of the outer tube 10, since a flow area of each of the bypass grooves 11a with respect to the amount of the solution is too small, a flow resistance of the solution flowing through the bypass groove 11a is increased. In this case, when a pushing speed of the plunger rod 70 exceeds a constant speed, the pressing force due to the advancement of the end stopper 50 is applied as a force of moving the middle stopper 40 forward, without contributing to the flowing of the solution in the bypass groove 11a. As a result, when the middle stopper 40 moves over the bypass section 11 to arrive at the distal end side tubular section, a large amount of solution remains in the rear chamber.

On the other hand, in the embodiment, since the cross-sectional area of the bypass groove 11a, i.e., the flow area of the solution, is minimally secured, the flowing of the solution in the bypass groove 11a is not interfered with. Accordingly, since careless advancement of the middle stopper 40 is prevented, all of the solution can be introduced into the front chamber without the solution remaining in the rear chamber.

Furthermore, since the depth F of the bypass groove 11a is 2.7% or more and 3.8% or less, or 2.1% or more and 3.3% or less of the inner diameter of the outer tube 10, the solution remaining in the bypass groove 11a can be eliminated.

That is, when the depth F of the bypass groove 11a exceeds 3.8% or 3.3% of the inner diameter of the outer tube 10, the bottom section of the bypass groove 11a is excessively spaced apart from the inner circumference of the outer tube 10, and thus the amount of the solution remaining in the bottom section is increased.

On the other hand, in the embodiment, since the depth F of the bypass groove 11*a* is set within the above-mentioned appropriate range, the solution remaining in the bypass groove 11*a* can be reduced to a minimum level. In addition, accordingly, fracture strength of the outer tube 10 can be secured at a high level.

Here, when the cross-sectional shape of the bypass groove 11*a* is rectangular, it is difficult to form the groove having the rectangular cross section in the glass inner wall, and two sharp corners formed in the rectangular shape may cause a remarkable decrease in the fracture strength of the outer tube. In addition, a corner of the bottom section of the bypass grove 11*a* causes the solution to remain in the groove. On the other hand, in the embodiment, since the cross-sectional shape of the bypass groove 11*a* is a substantially triangular shape, influence applied to the fracture strength of the outer tube becomes slight and the solution which remains in the groove is minimized.

Figure 8A:
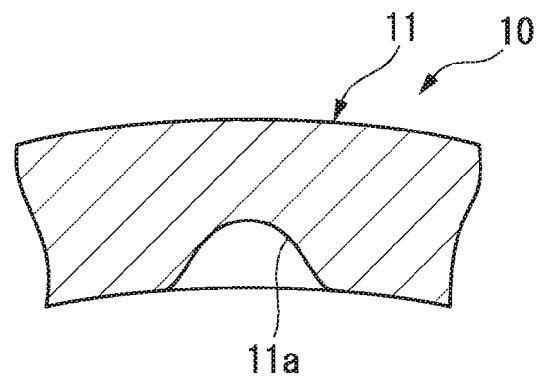
FIG. 8A is a view for describing an example of shapes of the bypass groove.
Figure 8B:
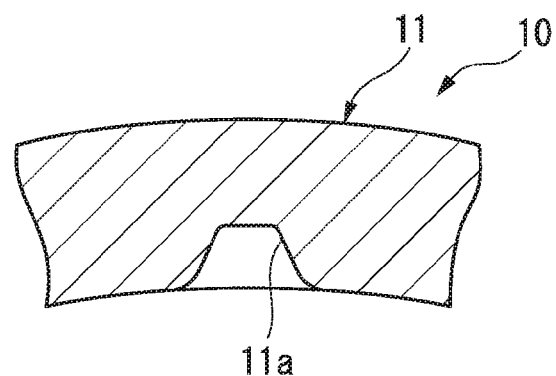
FIG. 8B is a view for describing an example of shapes of the bypass groove.
Figure 8C:
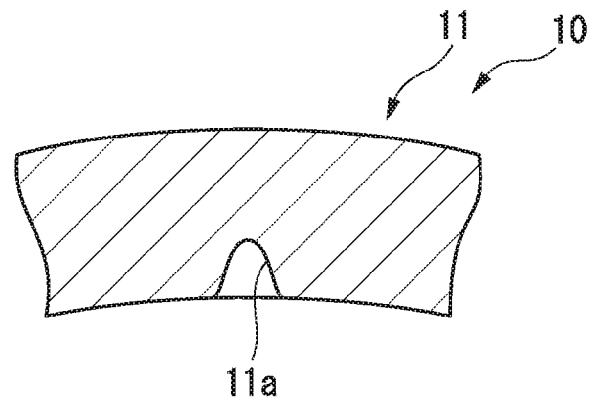
FIG. 8C is a view for describing an example of shapes of the bypass groove.

In addition, the cross-sectional shape of the bypass groove 11*a* may be, for example, a substantially semi-circular shape as shown in FIG. 8A or a substantially trapezoidal shape as shown in FIG. 8B. Further, as shown in FIG. 8C, the triangular shape may be substantially an isosceles triangular shape having a smaller top angle. Regardless of the cross-sectional shape of the bypass groove, as shown in FIGS. 8A to 8C, since the corners are not sharp but rounded, a decrease in the fracture strength of the outer tube is suppressed, and the solution remaining in the groove can be reduced while the groove can be formed easily.

In this way, in comparison with the case in which the cross-sectional shape of the bypass groove 11*a* is rectangular, the remaining solution in the groove can be reduced.

Further, in the embodiment, since the total cross-sectional area, which is the sum of the cross-sectional areas of the plurality of bypass grooves 11*a*, is set to 0.8% to 2.4% of the inner circumferential cross-sectional area of the outer tube 10 when the outer tube has an inner diameter of 10 mm or less, or set to 0.65% to 2.15% when the outer tube has an inner diameter of 10.1 mm or more, the large amount of solution remaining in the bypass groove 11*a* can be eliminated.

That is, since the total cross-sectional area, which is the sum of the cross-sectional areas of the plurality of bypass grooves 11*a*, has a large flow resistance of the solution in the bypass grove 11*a* when the inner circumferential cross-sectional area of the outer tube 10 is smaller than 0.8% or 0.65%, the middle stopper may advance before all of the solution is introduced into the front end side of the middle stopper via the bypass groove 11*a*.

In contrast, in the embodiment, as the total cross-sectional area of the bypass groove 11*a* is set to the above-described range, the aforementioned inconvenience can be overcome.

Hereinabove, while the two-chamber type combined container-syringe 100 according to the embodiment of the present invention has been described in detail, the present invention is not limited thereto but some design changes may be made without departing from the technical spirit of the present invention.

Hereinafter, examples will be described.

EXAMPLE 1

In the two-chamber type combined container-syringe in which the diameter of the outer tube is 8.65 mm, the inner diameter is 6.85 mm, the length of the bypass groove is 10 mm, the inner circumferential cross-sectional area is 36.83 mm$^2$, and the length of the inner circumference is 21.5 mm, experiments investigating movement of the middle stopper while varying the moving speed of the plunger rod were performed by variously changing the number, the depth, the width, and the cross-sectional area of the bypass grooves. The moving speeds of the plunger rod were from 10 mm/sec to 100 mm/sec at intervals of 10 mm/sec. Experiments are represented in Table 1. In Table 1, ○ represents qualification (no advancement of the middle stopper) and × represents disqualification (advancement of the middle stopper)

TABLE 1

| Sample no. | Bypass groove | | | Experiments on movement of middle stopper (Experiment speed: mm/sec) | | | | | | | | | |
|---|---|---|---|---|---|---|---|---|---|---|---|---|---|
| | Number | Depth (mm) | Width (mm) | Cross-sectional area (mm$^2$) | 10 | 20 | 30 | 40 | 50 | 60 | 70 | 80 | 90 | 100 |
| 1 | 5 | 0.19 | 0.47 | 0.051 | ○ | ○ | × | × | × | × | × | × | × | × |
| 2 | 5 | 0.24 | 0.45 | 0.057 | ○ | ○ | × | × | × | × | × | × | × | × |
| 3 | 6 | 0.18 | 0.43 | 0.046 | ○ | × | × | × | × | × | × | × | × | × |
| 4 | 6 | 0.19 | 0.44 | 0.051 | ○ | ○ | × | × | × | × | × | × | × | × |
| 5 | 6 | 0.17 | 0.58 | 0.054 | ○ | ○ | × | × | × | × | × | × | × | × |
| 6 | 8 | 0.17 | 0.50 | 0.055 | ○ | ○ | × | × | × | × | × | × | × | × |
| 7 | 8 | 0.23 | 0.51 | 0.064 | ○ | ○ | ○ | × | × | × | × | × | × | × |
| 8 | 8 | 0.23 | 0.62 | 0.078 | ○ | ○ | ○ | ○ | ○ | ○ | × | × | × | × |
| 9 | 10 | 0.24 | 0.55 | 0.081 | ○ | ○ | ○ | ○ | ○ | ○ | ○ | × | × | × |
| 10 | 10 | 0.26 | 0.59 | 0.087 | ○ | ○ | ○ | ○ | ○ | ○ | ○ | ○ | ○ | ○ |

Conventionally, when the two-chamber type combined container-syringe is used, the moving speed of the plunger rod is about 10 mm/sec. However, even when the user uses the plunger rod at a speed exceeding the moving speed, the middle stopper should not advance from the bypass section. In consideration of this, in practice, it is preferable that the middle stopper not advance from the bypass section even when the moving speed of the plunger rod is 20 mm/sec. Products that satisfy a condition that the middle stopper not advance even when the moving speed of the plunger rod is 20 mm/sec were classified as lower limit qualified products. In addition, products that satisfy a condition that the middle stopper not advance even when the plunger rod is moved at a largest moving speed (100 mm/sec) were classified as upper limit qualified products.

Meanwhile, products in which the middle stopper advances when the moving speed of the plunger rod is 20 mm/sec were classified as lower limit disqualified products. Details are represented in Table 2.

TABLE 2

| Classification of qualified products | Sample no. | Bypass groove | | | | Cross-sectional area ratio (%) | Depth/inner diameter (%) | Width/inner diameter (%) | Total cross-sectional area ratio | |
|---|---|---|---|---|---|---|---|---|---|---|
| | | Number | Depth (mm) | Bottom width (mm) | Cross-sectional area (mm²) | | | | Number × cross-sectional area (mm²) | Ratio (%) |
| Lower limit qualified products | 4 | 6 | 0.19 | 0.44 | 0.051 | 0.138 | 2.77 | 6.45 | 0.306 | 0.83 |
| Upper limit qualified products | 10 | 10 | 0.26 | 0.59 | 0.087 | 0.236 | 3.79 | 8.61 | 0.870 | 2.36 |
| Lower limit disqualified products | 3 | 6 | 0.18 | 0.43 | 0.046 | 0.124 | 2.62 | 6.28 | 0.276 | 0.75 |

EXAMPLE 2

In the two-chamber type combined container-syringe in which the diameter of the outer tube is 12.5 mm, the inner diameter is 10.5 mm, the length of the bypass groove is 10 mm, the inner circumferential cross-sectional area is 86.54 mm², and the length of the inner circumference is 33.0 mm, experiments investigating advancement of the middle stopper while varying the moving speed of the plunger rod were performed by variously changing the number, the depth, the width, and the cross-sectional area of the bypass grooves. The moving speeds of the plunger rod were from 10 mm/sec to 100 mm/sec at intervals of 10 mm/sec. Experiment results are represented in Table 3. In Table 3, ○ represents qualification (no advancement of the middle stopper) and × represents disqualification (advancement of the middle stopper).

TABLE 3

| Sample no. | Bypass groove | | | | Experiments on movement of middle stopper (Experiment speed: mm/sec) | | | | | | | | | |
|---|---|---|---|---|---|---|---|---|---|---|---|---|---|---|
| | Number | Depth (mm) | Width (mm) | Cross-sectional area (mm²) | 10 | 20 | 30 | 40 | 50 | 60 | 70 | 80 | 90 | 100 |
| 1 | 5 | 0.23 | 0.73 | 0.113 | ○ | ○ | × | × | × | × | × | × | × | × |
| 2 | 5 | 0.28 | 0.81 | 0.130 | ○ | ○ | ○ | × | × | × | × | × | × | × |
| 3 | 6 | 0.18 | 0.81 | 0.087 | ○ | × | × | × | × | × | × | × | × | × |
| 4 | 6 | 0.25 | 0.77 | 0.117 | ○ | ○ | ○ | × | × | × | × | × | × | × |
| 5 | 6 | 0.28 | 0.69 | 0.129 | ○ | ○ | ○ | ○ | ○ | × | × | × | × | × |
| 6 | 8 | 0.19 | 0.83 | 0.092 | ○ | ○ | × | × | × | × | × | × | × | × |
| 7 | 8 | 0.20 | 0.87 | 0.108 | ○ | ○ | ○ | ○ | ○ | ○ | ○ | × | × | × |
| 8 | 8 | 0.20 | 0.79 | 0.093 | ○ | ○ | ○ | ○ | × | × | Stop | × | × | × |
| 9 | 10 | 0.28 | 0.79 | 0.135 | ○ | ○ | ○ | ○ | ○ | ○ | ○ | ○ | ○ | ○ |
| 10 | 12 | 0.27 | 0.63 | 0.106 | ○ | ○ | ○ | ○ | ○ | ○ | ○ | × | × | × |
| 11 | 12 | 0.26 | 0.70 | 0.107 | ○ | ○ | ○ | ○ | ○ | ○ | ○ | ○ | × | × |

Similarly, the lower limit qualified products, the upper limit qualified products, and the lower limit disqualified products were determined based on Table 3.

Details are represented in Table 4

TABLE 4

| Classification of qualified products | Sample no. | Bypass groove | | | | Cross-Sectional area ratio (%) | Depth/inner diameter (%) | Width/inner diameter (%) | Total cross-sectional area ratio | |
|---|---|---|---|---|---|---|---|---|---|---|
| | | Number | Depth (mm) | Bottom width (mm) | Cross-Sectional area (mm²) | | | | Number × cross-sectional area (mm²) | Ratio (%) |
| Lower limit qualified products | 1 | 5 | 0.23 | 0.73 | 0.113 | 0.130 | 2.19 | 6.95 | 0.565 | 0.65 |
| Upper limit qualified products | 9 | 10 | 0.28 | 0.79 | 0.135 | 0.155 | 2.66 | 7.52 | 1.350 | 1.55 |
| Lower limit disqualified products | 3 | 6 | 0.18 | 0.81 | 0.087 | 0.100 | 1.71 | 7.71 | 0.522 | 0.60 |

EXAMPLE 3

In the two-chamber type combined container-syringe in which the diameter of the outer tube is 16.0 mm, the inner diameter is 14.0 mm, the length of the bypass groove is 10 mm, the inner circumferential cross-sectional area is 153.86 mm$^2$, and the length of the inner circumference is 44.0 mm, experiments investigating advancement of the middle stopper while varying the moving speed of the plunger rod were performed by variously changing the number, the depth, the width, and the cross-sectional area of the bypass grooves. The moving speeds of the plunger rod were from 10 mm/sec to 100 mm/sec at intervals of 10 mm/sec. Experiments are represented in Table 5. In Table 5, ○ represents qualification (no advancement of the middle stopper) and × represents disqualification (advancement of the middle stopper)

TABLE 5

| Sample no. | Bypass groove | | | | Experiments on movement of middle stopper (Experiment speed: mm/sec) | | | | | | | | | |
|---|---|---|---|---|---|---|---|---|---|---|---|---|---|---|
| | Number | Depth (mm) | Width (mm) | Cross-sectional area (mm$^2$) | 10 | 20 | 30 | 40 | 50 | 60 | 70 | 80 | 90 | 100 |
| 1 | 10 | 0.20 | 0.84 | 0.095 | x | x | x | x | x | x | x | x | x | x |
| 2 | 10 | 0.48 | 0.87 | 0.265 | ○ | ○ | ○ | ○ | ○ | ○ | ○ | ○ | ○ | x |
| 3 | 12 | 0.48 | 0.90 | 0.262 | ○ | ○ | ○ | ○ | ○ | ○ | ○ | ○ | ○ | ○ |
| 4 | 14 | 0.28 | 0.56 | 0.120 | ○ | ○ | x | x | x | x | x | x | x | x |
| 5 | 14 | 0.29 | 0.70 | 0.131 | ○ | ○ | ○ | ○ | x | x | x | x | x | x |
| 6 | 14 | 0.32 | 0.86 | 0.165 | ○ | ○ | x | x | x | x | x | x | x | x |
| 7 | 14 | 0.35 | 0.84 | 0.180 | ○ | ○ | ○ | ○ | ○ | ○ | ○ | x | x | x |
| 8 | 14 | 0.45 | 0.88 | 0.237 | ○ | ○ | ○ | ○ | ○ | ○ | ○ | ○ | ○ | ○ |
| 9 | 20 | 0.26 | 0.73 | 0.117 | ○ | ○ | ○ | x | x | x | x | x | x | x |
| 10 | 20 | 0.24 | 0.81 | 0.122 | ○ | ○ | ○ | ○ | x | x | x | x | x | x |

Similarly, the lower limit qualified products, the upper limit qualified products, and the lower limit disqualified products were determined based on Table 5.

Details are represented in Table 6

TABLE 6

| Classification of qualified products | Sample no. | Bypass groove | | | | Cross-sectional area ratio (%) | Depth/inner diameter (%) | Width/inner diameter (%) | Total cross-sectional area ratio | |
|---|---|---|---|---|---|---|---|---|---|---|
| | | Number | Depth (mm) | Bottom width (mm) | Cross-Sectional area (mm$^2$) | | | | Number × cross-sectional area (mm$^2$) | Ratio (%) |
| Lower limit qualified products | 6 | 14 | 0.32 | 0.86 | 0.165 | 0.107 | 2.28 | 6.14 | 2.31 | 1.50 |
| Upper limit qualified products | 8 | 14 | 0.45 | 0.88 | 0.237 | 0.154 | 3.21 | 6.28 | 3.318 | 2.15 |
| Lower limit disqualified products | 1 | 10 | 0.20 | 0.84 | 0.095 | 0.062 | 1.43 | 6.00 | 0.95 | 0.62 |

[Considerations]

[With Respect to Cross-Sectional Area of each Bypass Groove]

Based on the above-mentioned experiment results, relations between the cross-sectional areas of the bypass groove and the qualification/disqualification are organized in Table 7.

TABLE 7

| | | Inner diameter of outer tube | | | | | |
|---|---|---|---|---|---|---|---|
| | | 6.85 mm | | 10.5 mm | | 14.0 mm | |
| | | Cross-sectional area of inner diameter (a) | | | | | |
| | | 36.83 mm$^2$ | | 86.54 mm$^2$ | | 153.86 mm$^2$ | |
| Qualified products | 20 mm/sec | 0.051 mm$^2$ | 0.138% | 0.113 mm$^2$ | 0.130% | 0.165 mm$^2$ | 0.107% |
| | 100 mm/sec | 0.087 mm$^2$ | 0.236% | 0.135 mm$^2$ | 0.155% | 0.237 mm$^2$ | 0.154% |
| Disqualified products | | 0.046 mm$^2$ | 0.124% | 0.087 mm$^2$ | 0.100% | 0.095 mm$^2$ | 0.062% |

From Table 7, it will be appreciated that, when the inner diameter of the outer tube is 6.85 mm, provided that the cross-sectional area of the bypass groove is 0.138% or more and 0.236% or less of the inner circumferential cross-sectional area of the outer tube, the solution can smoothly flow through the bypass groove without advancement of the middle stopper when the moving speed of the plunger rod is 20 mm/sec to 100 mm/sec. In addition, such an effect may be considered to be similarly exhibited even when the cross-sectional area of the bypass groove is within a range of 0.13% or more and 0.24% or less of the inner circumferential cross-sectional area of the outer tube. Furthermore, this effect is not limited to the case in which the inner diameter is 6.85 mm, the same effect can be considered to be exhibited even when the inner diameter of the outer tube is 6.0 mm or more and 10.0 mm or less.

In addition, it will be appreciated that, when the inner diameter of the outer tube is 10.5 mm or 14.0 mm, provided that the cross-sectional area of the bypass groove is 0.107% or more and 0.155% or less of the inner circumferential cross-sectional area of the outer tube, the solution can smoothly flow through the bypass groove without advancement of the middle stopper when the moving speed of the plunger rod is 20 mm/sec to 100 mm/sec. In addition, such an effect may be considered to be similarly exhibited even when the cross-sectional area of the bypass groove is within a range of 0.105% or more and 0.155% or less of the inner circumferential cross-sectional area of the outer tube. Furthermore, this effect is not limited to the case in which the inner diameter is 10.5 mm or 14.0 mm, the same effect can be considered to be exhibited even when the inner diameter of the outer tube is 10.1 mm or more and 18.0 mm or less.

[With Respect to Total Cross-Sectional Area of Bypass Grooves]

Based on the above-mentioned experiment results, relations between the total cross-sectional area of the bypass groove and the qualification/disqualification are organized in Table 8 the bypass groove is within a range of 0.8% or more and 2.4% or less of the inner circumferential cross-sectional area of the outer tube. Furthermore, this effect is not limited to the case in which the inner diameter of the outer tube is 6.85 mm, the same effect can be considered to be exhibited even when the inner diameter is 6.0 mm or more and 10.0 mm or less.

In addition, it will be appreciated that, when the inner diameter of the outer tube is 10.5 mm or 14.0 mm, provided that the total cross-sectional area of the bypass groove is 0.65% or more and 2.15% or less of the inner circumferential cross-sectional area of the outer tube, the solution can smoothly flow through the bypass groove without advancement of the middle stopper when the moving speed of the plunger rod is 20 mm/sec to 100 mm/sec. In addition, this effect is not limited to the case in which the inner diameter of the outer tube is 10.5 mm or 14.0 mm, the same effect can be considered to be exhibited even when the inner diameter is 10.1 mm or more and 18.0 mm or less.

[With Respect to Depth of Bypass Groove]

Based on the above-mentioned experiment results, relations between the depth of the bypass groove and the qualification/disqualification are organized in Table 9

TABLE 9

| Inner diameter of outer tube | | 6.85 mm | | 10.5 min | | 14.0 mm | |
|---|---|---|---|---|---|---|---|
| Qualified products | 20 mm/sec | 0.19 mm | 2.77% | 0.23 mm | 2.19% | 0.32 mm | 2.28% |
| | 100 mm/sec | 0.26 mm | 3.79% | 0.28 mm | 2.66% | 0.45 mm | 3.21% |
| Disqualified products | | 0.18 mm | 2.62% | 0.18 mm | 1.71% | 0.20 mm | 1.43% |

From Table 9, it will be appreciated that, when the inner diameter of the outer tube is 6.85 mm, provided that the depth of the bypass groove is 2.77% or more and 3.79% or less of the inner diameter of the outer tube, the solution can smoothly flow through the bypass groove without advancement of the

TABLE 8

| | | Inner diameter of outer tube | | | | | | | | | |
|---|---|---|---|---|---|---|---|---|---|---|---|
| | | 6.85 mm | | | | 10.5 mm | | | 14.0 mm | | |
| | | Cross-sectional area of inner diameter | | | | | | | | | |
| | | 36.83 mm² | | | | 86.54 mm² | | | 153.86 mm² | | |
| | | Bypass groove | | | | | | | | | |
| | | Cross-sectional area of one groove (mm²) | Number | Total cross-sectional area (mm²) | Ratio (%) | Cross-sectional area of one groove (mm²) | Number | Total cross-sectional area (mm²) | Ratio (%) | Cross-sectional area of one groove (mm²) | Number | Total Cross-Sectional Area (mm²) | Ratio (%) |
| Qualified products | 20 mm/sec | 0.051 | 6 | 0.306 | 0.83 | 0.113 | 5 | 0.565 | 0.65 | 0.165 | 14 | 2.310 | 1.50 |
| | 100 mm/sec | 0.087 | 10 | 0.870 | 2.36 | 0.135 | 10 | 1.350 | 1.55 | 0.237 | 14 | 3.318 | 2.15 |
| Disqualified products | | 0.046 | 6 | 0.276 | 0.75 | 0.087 | 6 | 0.522 | 0.60 | 0.095 | 10 | 0.950 | 0.62 |

From Table 8, it will be appreciated that, when the inner diameter of the outer tube is 6.85 mm, provided that the total cross-sectional area of the bypass groove is 0.83% or more and 2.36% or less of the inner circumferential cross-sectional area of the outer tube, the solution can smoothly flow through the bypass groove without advancement of the middle stopper when the moving speed of the plunger rod is 20 mm/sec to 100 mm/sec. In addition, such an effect may be considered to be similarly exhibited even when the total cross-sectional area of middle stopper when the moving speed of the plunger rod is 20 mm/sec to 100 mm/sec. In addition, such an effect may be considered to be similarly exhibited even when the depth of the bypass groove is 2.7% or more and 3.8% or less of the inner diameter of the outer tube. Furthermore, this effect is not limited to the case in which the inner diameter of the outer tube is 6.85 mm, the same effect can be considered to be exhibited even when the inner diameter is 6.0 mm or more and 10.0 mm or less.

In addition, it will be appreciated that, when the inner diameter of the outer tube is 10.5 mm or 14.0 mm, provided that the depth of the bypass groove is 2.19% or more and 3.21% or less of the inner diameter of the outer tube, the solution can smoothly flow through the bypass groove without advancement of the middle stopper when the moving speed of the plunger rod is 20 mm/sec to 100 mm/sec. In addition, the same effect can be considered to be exhibited even when the depth of the bypass groove is within a range of 2.1% or more and 3.3% or less of the inner diameter of the outer tube. Furthermore, this effect is not limited to the case in which the inner diameter of the outer tube is 10.5 mm or 14.0 mm, the same effect can be considered to be exhibited even when the inner diameter is 10.1 mm and more or 18.0 mm or less.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A two-chamber type combined container-syringe, comprising:
    an outer tube formed in a tubular shape having a uniform inner diameter about an axis thereof in an axial direction and provided with a bypass groove concaved from an inner circumferential surface in a portion in the axial direction;
    a front assembly installed at a distal end of the outer tube;
    a finger grip installed at a rear end of the outer tube;
    a front stopper fitted into a distal end side of the bypass groove in the outer tube;
    a middle stopper fitted into a rear end side of the bypass groove in the outer tube and configured to seal a preparation with the front stopper;
    an end stopper fitted into the rear end side of the middle stopper in the outer tube and configured to seal a solution with the middle stopper; and
    a plunger rod inserted through the finger grip to be connected to the end stopper from the rear end side,
    wherein the inner diameter of the outer tube is a value that falls between the range of 6.0 to 10.0 mm,
    the plurality of bypass grooves are formed in a circumferential direction of the axis at intervals,
    a cross-sectional area of the bypass groove perpendicular to the axis is a value that falls between the range of 0.13% to 0.24% of an inner circumferential cross-sectional area of the outer tube perpendicular to the axis, and
    a depth of the bypass groove concaved from the inner circumferential surface is a value that falls between the range of 2.7% to 3.8% of the inner diameter of the outer tube.

2. The two-chamber type combined container-syringe according to claim 1, wherein a sum of the cross-sectional areas of the entire bypass grooves perpendicular to the axis is 0.8% to 2.4% of an inner circumferential cross-sectional area of the outer tube perpendicular to the axis.

3. The two-chamber type combined container-syringe according to claim 1, wherein an interval of the bypass grooves neighboring in the circumferential direction of the axis and disposed at a center in the circumferential direction is within a range of 2.0 mm to 7.3 mm.

4. The two-chamber type combined container-syringe according to claim 1, wherein the cross-sectional shape of the bypass groove perpendicular to the axis is any one of a triangular shape, a trapezoidal shape, a semi-circular shape, or a combination thereof.

5. The two-chamber type combined container-syringe according to claim 1, wherein the outer tube is formed of glass or a synthetic resin.

6. A two-chamber type combined container-syringe, comprising:
    an outer tube formed in a tubular shape having a uniform inner diameter about an axis thereof in an axial direction and provided with a bypass groove concaved from an inner circumferential surface in a portion in the axial direction;
    a front assembly installed at a distal end of the outer tube;
    a finger grip installed at a rear end of the outer tube;
    a front stopper fitted into a distal end side of the bypass groove in the outer tube;
    a middle stopper fitted into a rear end side of the bypass groove in the outer tube and configured to seal a preparation with the front stopper;
    an end stopper fitted into the rear end side of the middle stopper in the outer tube and configured to seal a solution with the middle stopper; and
    a plunger rod inserted through the finger grip to be connected to the end stopper from the rear end side,
    wherein the inner diameter of the outer tube is a value that falls between the range of 10.1 to 18.0 mm,
    the plurality of bypass grooves are formed in a circumferential direction of the axis at intervals,
    a cross-sectional area of the bypass groove perpendicular to the axis is a value that falls between the range of 0.105% to 0.160% of an inner circumferential cross-sectional area of the outer tube perpendicular to the axis, and
    a depth of the bypass groove concaved from the inner circumferential surface is a value that falls between the range of 2.1% to 3.3% of the inner diameter of the outer tube.

7. The two-chamber type combined container-syringe according to claim 6, wherein a sum of the cross-sectional areas of the entire bypass grooves perpendicular to the axis is 0.65% to 2.15% of an inner circumferential cross-sectional area of the outer tube perpendicular to the axis.

* * * * *